United States Patent
Furukawa et al.

(10) Patent No.: US 6,875,875 B2
(45) Date of Patent: Apr. 5, 2005

(54) PROCESS FOR PREPARING GLYCIDYLPHTHALIMIDE

(75) Inventors: Yoshiro Furukawa, Osaka (JP); Yasushi Miki, Osaka (JP)

(73) Assignee: Daiso Co., Ltd., Osaka-Fu (JP)

(*) Notice: Subject to any disclaimer, the term of this patent is extended or adjusted under 35 U.S.C. 154(b) by 0 days.

(21) Appl. No.: 10/669,743

(22) Filed: Sep. 25, 2003

(65) Prior Publication Data

US 2004/0087802 A1 May 6, 2004

(30) Foreign Application Priority Data

Sep. 25, 2002 (JP) ........................................ 2002-279277
Mar. 12, 2003 (JP) ........................................ 2003-066011

(51) Int. Cl.[7] .............................................. C07D 45/02
(52) U.S. Cl. ...................................................... 548/465
(58) Field of Search ........................................ 548/465

(56) References Cited

U.S. PATENT DOCUMENTS

| | | |
|---|---|---|
| 4,599,346 A | 7/1986 | Schickaneder et al. |
| 5,608,110 A | 3/1997 | Ramalingam et al. |

FOREIGN PATENT DOCUMENTS

| | | |
|---|---|---|
| DE | 33 26 545 | 1/1985 |
| WO | 99/24393 | 5/1999 |

OTHER PUBLICATIONS

M. Weizmann et al., "No. 40—Action of hydracids on the epihydrine–phthalimide", Bulletin du Societe de la Chimie, pp. 356–361, Feb. 17, 1930.

Yoshihito Hayashi et al., "Synthesis, Characterization, and Reversible Oxygenation of $\mu$–Alkoxo Diiron(II) Complexes with the Dinucleating Ligand N, N,N', N'–Tetrakis{(6–methyl–2–pyridyl)methyl}–1, 3–diamino–propan–2–olate", J. Am. Chem. Soc., 117, 11220–11229, 1995.

Maryam Zakerina et al., "The Syntheses of Purine and Pyrimidine Secoribo–nucleosides: Acyclo–uridine Derivative of Cyclophosphamide", Helvetica Chimica Acta, vol. 73, pp. 912–915, 1990.

Dariusz Bogdal et al., "Remarkable Fast Microwave–assisted N–Alkylation of Phthalimde in Dry Media", Synlett, pp. 873–874, Sep. 1996.

*Primary Examiner*—Joseph K. McKane
*Assistant Examiner*—R. Waller
(74) *Attorney, Agent, or Firm*—Wenderoth, Lind & Ponack, L.L.P.

(57) ABSTRACT

A process for preparing glycidylphtalimide or it optically active compound by reacting a phthalimide alkalimetal salt with an epihalohydrin or an optically active epihalohydrin in an alcohol solvent; or by reacting phthalimide with an epihalohydrin or an optically active epihalohydrin in the presence of an alkali metal carbonate, an alkali metal hydrogencarbonate or a quaternary ammonium salt to obtain a N-(3-halogeno-2-hydroxypropyl)phthalimide and then by cyclizing the product with an alkali metal alkoxide.

20 Claims, No Drawings

PROCESS FOR PREPARING GLYCIDYLPHTHALIMIDE

BACKGROUND OF THE INVENTION

The present invention relates to a process for preparing glycidylphthalimide, especially optically active glycidylphthalimide, which is useful as an intermediate for preparing medicines, agrochemicals or physiologically active compounds.

PRIOR ART

Glycidylphthalimide, especially optically active glycidylphthalimide is utilizable as an important intermediate for preparing many kinds of optically active medicines.

Generally, optically active medicines and intermediates thereof are required of 98% e.e. with optical purity. Therefore it is very important to establish the process for preparation of optically active glycidylphthalimide having optically high purity easily.

As general methods for preparing racemic glycidylphthalimide, a method for preparing it by refluxing potassium phthalimide in racemic epichlorohydrin solvent (J. Am. Chem. Soc. Vol. 117, p 11220–11229(1995): abbreviated as Reference 1) and a method for preparing it by reacting an equal molar quantity of potassium phthalimide and a racemic epihalohydrin in DMF (Helv. Chim. Acta Vol. 73, p 912–915(1990): abbreviated as Reference 2) have been developed. Furthermore, a method for preparing it by reacting phthalimide and racemic epichlorohydrin in tetra-n-butylammonium iodide and potassium carbonate in a microwave oven is described in Synlett p 873–874(1996) (abbreviated as Reference 3).

On the other hand in regard to methods for preparing optically active glycidylphthalimide, a method for preparing it by following steps (a) to (c): (a) refluxing phthalimide in optically active epichlorohydrin solvent to obtain optically active N-(3-chloro-2-hydroxypropyl)phthalimide, (b) isolating and purifying the compound and then (c) cyclizing the compound with sodium hydride is described in U.S. Pat. No. 5,608,110. In WO 99/24393, (S)-glycidylphthalimide is described, but there is no description on the method for preparing it.

According to the above methods for preparing racemic glycidylphthalimide described in Reference 1, when potassium phthalimide and an optically active epihalohydrin in the amount of the solvent is reacted under refluxing, optical purity of the epihalohydrin decreases and therefore, optical purity of glycidylphthalimide produced therein decreases. When optically active epichlorohydrin (99% e.e.) and potassium phthalimide are reacted in DMF, racemization proceeds to give optically active glycidylphthalimide with poor optical purity (63% e.e.) (See Coperative example 1).

On the other hand, the object compound is not obtained in good yield when the reaction is carried out in a microwave oven according to the method described in Reference 3. According to the method of U.S. Pat. No. 5,608,110, an intermediate, N-(3-chloro-2-hydroxypropyl)phthalimide must be isolated and the yield thereof and the object compound are not satisfactory.

The present inventors have extensively studied to solve the above problem and it have been found that by reacting an optically active epihalohydrin and an alkali metal phthalimide in an alcohol as a solvent, optically active glycidylphthalimide is easily obtainable in good yield and with optically high purity. Furthermore, it has been found that by reacting a racemic epihalohydrin and an alkali metal phthalimide, racemic glycidylphthalimide is also easily obtainable in good yield.

In addition, it has been found that racemic glycidylphthalimide and its optically active compound are easily obtainable in good yield and optically active glycidylphthalimide is obtainable with optically high purity, by reacting phthalimide and an epihalohydrin or an optically active epihalohydrin in an organic solvent in the presence of an alkali metal carbonate, an alkali metal hydrogencarbonate or a quaternary ammonium salt to obtain a N-(3-halogeno-2-hydroxypropyl)phthalimide and then by cyclizing the compound with an alkali metal alkoxide, too.

Namely the present invention relates to a process for preparing a glycidylphthalimide represented by the following formula (1):

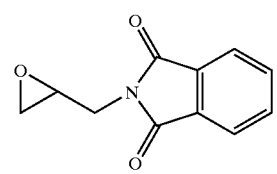

(1)

which comprises reacting in an alcohol solvent an alkali metal phthalimide represented by the following formula (2):

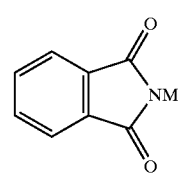

(2)

wherein M is an alkali metal, with an epihalohydrin represented by the following formula (3):

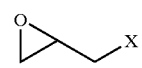

(3)

wherein X is a halogen atom; or reacting phthalimide and an epihalohydrin (3) in an organic solvent in the presence of an alkali metal carbonate, an alkali metal hydrogencarbonate or a quaternary ammonium salt (4) represented by the following formula:

$$R_1 R_2 R_3 R_4 N^+ X^- \qquad (4)$$

wherein $R_1$, $R_2$, $R_3$ and $R_4$ are the same or different, $C_{1-16}$ alkyl, $C_{2-16}$ alkenyl, aryl-alkyl($C_{1-16}$) or aryl, and X is chloro ion, bromo ion, iodo ion, hydrogensulfate ion or hydroxy ion, to prepare a N-(3-halogeno-2-hydroxypropyl)phthalimide represented by the following formula (5):

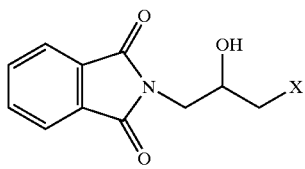

(5)

wherein X is the same as defined above,
and then by cyclizing the compound (5) with an alkali metal alkoxide.

The present invention relates to a process for preparing glycidylphtalimide (1) which comprises reacting in an alcohol solvent an alkali metal phthalimide (2) with an epihalohydrin (This invention refers to process (A)).

Especially the present invention relates to a process for preparing optically active glycidylphthalimide (1) which comprises reacting an alkali metal phthalimide (2) with an optically active epihalohydrin (3) in an alcohol solvent.

The present invention also relates to the above mentioned process (A), wherein the process is carried out in the presence of a quaternary ammonium salt (4).

The present invention relates to a process for preparing glycidylphtalimide (1) which comprises reacting phthalimide and an epihalohydrin (3) in an organic solvent in the presence of an alkali metal carbonate, an alkali metal hydrogencarbonate or a quaternary ammonium salt (4) to prepare a N-(3-halogeno-2-hydroxypropyl)phthalimide (5) and then by cyclizing the compound (5) with an alkali metal alkoxide (This invention refers to process (B)).

The present invention relates to a process for preparing glycidylphtalimide (1) which comprises carrying out the above process (B) without isolating a N-(3-halogeno-2-hydroxypropyl)phthalimide (5) prepared in the first step, namely one pot method.

Especially the present invention relates to process (B) for preparing optically active glycidylphthalimide (1) which comprises reacting phthalimide with an optically active epihalohydrin, especially optically active epichlorohydrin.

The present invention also relates to a process for preparing a N-(3-halogeno-2-hydroxypropyl)phthalimide (5) which comprises reacting phthalimide and an epihalohydrin (3) in an organic solvent in the presence of an alkali metal carbonate, an alkali metal hydrogencarbonate or a quaternary ammonium salt (4). Furthermore, the present invention relates to a process for preparing an optically active N-(3-halogeno-2-hydroxypropyl)phthalimide (5) which comprises reacting phthalimide with an optically active epihalohydrin in an organic solvent.

The alkali metal phthalimide (2) used in the present invention relating to process (A) includes the compound in which an alkali metal is bound with nitrogen atom consisting of an imido group of the compound, such as sodium phthalimide, potassium phthalimide, cesium phthalimide, and preferably potassium phthalimide.

The epihalohydrin (3) used in the present invention relating to process (A) includes epichlorohydrin, epibromohydrin and epiiodohydrin, preferably optically active isomer thereof, especially preferably an optically active epihalohydrin. The amount of the epihalohydrin is 1 to 4 moles to the alkali metal phthalimide (2), preferably 2 to 3 moles.

The alcohol solvent used in the present invention relating to process (A) includes primary alcohols, such as methanol, ethanol, 1-propanol, 1-butanol, 1-pentanol, 1-hexanol, etc., secondary alcohols, such as isopropanol, 2-butanol, 2-pentanol, 3-pentanol, 2-hexanol, cyclohexanol, 2-heptanol, 3-heptanol, etc., tertiary alcohols, such as tert-butanol, tert-pentanol, etc., preferably secondary or tertiary alcohols, more preferably isopropanol, 2-butanol and tert-butanol.

The amount of the alcohol solvent is preferably used 2 to 20 times (w/w) that of the alkali metal phthalimide (2).

The quaternary ammonium salt used in the present invention relating to process (A) is not limited, but includes benzyltrimethylammonium chloride, diallyldimethylammonium chloride, benzyltrimethylammonium bromide, n-octyltrimethylammonium bromide, stearyltrimethylammonium bromide, cetyldimethylammonium bromide, tetra n-butylammonium iodide, β-methylcholinium iodide, tetra n-butylammonium hydrogensulfate, phenyltrimethylammonium hydoxide, etc.

The reaction relating to process (A) is promoted by addition of a quaternary ammonium salt (4) in the reaction system and therefore, the yield of glycidylphthalimide (1) or its optically active compound can be increased.

The amount of the quatenary ammonium salt (4) is catalytic amount to the alkali metal phthalimide (2), preferably 0.005 to 0.1 mole.

The reaction relating to process (A) is preferably carried out at −10 to 60° C., more preferably 0 to 30° C. When the reaction is carried out at below −10° C. the reaction is restrained (controlled) and it is not desirable. When the reaction is carried out beyond 60° C., the side reaction proceeds and therefore, it causes decrease of the yield on the object compound (1) and, in case that an epihalohydrin used is optically active, racemization of the compound proceeds and it causes decrease of optical purity of optically active glycidylphthlimide (1).

One of the merits of the present invention relating to process (A) is to that glycidylphthalimide (1), especially optically active glycidylphthalimide is obtained in good yield with highly optical purity by such a very simple procedure as removing the alcohol solvent and washing a solvent for extraction after the reaction is completed.

The solvent for extraction of the object compound is not limited as long as the compound is dissolved in said solvent, but includes acetates, such as methyl acetate, ethyl acetate, etc., and halogeno compounds, such as methylene chloride, chloroform, 1,2-dichloroethane, etc. The product may be, if necessary, purified by crystallization and column chromatography.

The epihalohydrin (3) used in the present invention relating to process (B) includes epichlorohydrin, epibromohydrin and epiiodohydrin, preferably optically active form thereof, especially preferably an optically active epihalohydrin. The amount of the epihalohydrin is 1 to 3 moles to the alkali metal phthalimide (2), preferably 1 to 2 moles.

The alkali metal carbonate used in the present invention relating to process (B) is not limited, but includes lithium carbonate, sodium carbonate, potassium carbonate and cesium carbonate, and the alkali metal hydrogencarbonate used in the present invention relating to process (B) is not limited, but includes lithium hydrogencarbonate, sodium hydrogencarbonate, potassium hydrogencarbonate and cesium hydrogencarbonate. These carbonate salts may be hydrous or anhydrous, but in case preparing optically active glycidylphthalimide, an anydrous carbonate salt is preferable. The amount of the alkali metal carbonate or the alkali metal hydrogencarbonate may be either stoichiometric amount or catalytic amount to phthalimide or, preferably 0.01 to 3 moles.

The quaternary ammonium salt used in the present invention relating to process (B) is the same as used in process (A).

The amount of the quatenary ammonium salt (4) is catalytic amount to the alkali metal phthalimide (2), preferably 0.005 to 0.1 mole. When the quatenary ammonium salt (4) is used together with the above alkali metal carbonate or alkali metal hydrogencarbonate, the reaction relating to process (B) is promoted to give the product in good yield.

The organic solvent used in the present invention relating to process (B) is not limited as long as it does not react with reactants (e.g., amines, carboxylic acid or a compound having glycidyl group), but in case preparing optically active glycidylphthalimide (1), alcohols, ethers and a mixture thereof are preferably used. The alcohol includes primary alcohols, such as methanol, ethanol, 1-propanol, 1-butanol, 1-pentanol, 1-hexanol, etc., secondary alcohols, such as isopropanol, 2-butanol, 2-pentanol, 3-pentanol, 2-hexanol, cyclohexanol, 2-heptanol, 3-heptanol, etc., and tertiary alcohols, such as tert-butanol, tert-pentanol, etc., preferably methanol, isopropanol and tert-butanol. The ether includes diethyl ether, dibutyl ether, tert-butyl methyl ether, 1,2-dimethoxyethane, 1,4-dioxane, tetrahydrofuran (THF), etc. The ratio of the mixture of the solvents is not limited. The amount of the solvent is preferably used 4 to 20 times (w/w) that of phthalimide.

The alkali metal alkoxide used in the present invention relating to process (B) (in 2nd step) includes sodium methoxide, potassium methoxide, sodium ethoxide, potassium ethoxide, sodium n-propoxide, potassium n-propoxide, sodium isopropoxide, potassium isopropoxide, sodium n-butoxide, potassium n-butoxide, sodium tert-butoxide, potassium tert-butoxide, sodium tert-amylate, potassium amylate, sodium n-hexylate, potassium n-hexylate, etc.

The alkali metal hydroxide should be added after phthalimide and an epihalohydrin (3) are completely condensed to give a N-(3-halogeno-2-hydroxypropyl)phthalimide. When the alkali metal alkoxide is added while phthalimide and an epihalohydrin is being condensed, the side reaction occurs and the yield of the object compound, especially the yield of the optically active compound decreases (See Coparative example 5). The alkali metal hydroxide is preferably added in several divided portions or is preferably gradually added to the reaction mixture after resolving it in an alcohol or an ether.

The reaction relating to process (B) is preferably carried out at −10 to 60° C., more preferably 0 to 50° C.

Furthermore, there are obtainable a N-(3-halogeno-2-hydroxypropyl)phthalimide (5) in good yield or its optically active compound in good yield with high optical purity by reacting phthalimide with an epihalohydrin (3) or an optically active epihalohydrin (3) in the presence of an alkali metal carbonate, an alkali metal hydrogencarbonate or a quaternary ammonium salt (4) in an organic solvent, preferably an alcohol or an ether and then by extracting and purifying the product by crystallization or column chromatography. Thus obtained N-(3-halogeno-2-hydroxypropyl) phthalimide (5) is very useful for an intermediate of glycidylphtalate or other compounds.

One of the merits of the present invention relating to process (B) is to that the process is carried out by using cheaper materials and cheaper solvents, and glycidylphthalimide (1), especially optically active glycidylphthalimide is obtained in good yield with highly optical purity by such a very simple procedure as the solvent is removed and the product is washed with the solvent for extraction after the reaction is completed. The solvent for extraction of the object compound is not limited as long as the compound is dissolved in said solvent, but includes acetates such as methyl acetate, ethyl acetate, etc., and halogeno compounds, such as methylene chloride, chloroform, 1,2-dichloroethane, etc. The product may be, if necessary, purified by crystallization and column chromatography.

Another of the merits of the present invention relating to process (B) is to that without isolation of a N-(3-halogeno-2-hydroxypropyl)phthalimide (5) or its optically active compound obtained by reacting phthalimide with an epihalohydrin (3) or an optically active epihalohydrin, the product is reacted with an alkali metal alkoxide to give glycidylphthalimide (1) or its optically activated compound. Using the one pot method the object compound (1) and its optically active compound are obtained in good yield and/or with optically high purity.

The present invention is explained by the following examples and comparative examples, but is not limited by those examples.

EXAMPLE 1

Into a reaction vessel were put potassium phthalimide (50.0 g, 0.27 mol), benzyltrimethylammonium chloride 5.00 g, 0.027 mol) and isopropanol (500 ml), and the mixture was cooled to 10° C. Thereto was added (R)-epichlorohydrin (74.9 g, 0.81 mol) and the mixture was stirred for 46 hours while being cooled. The solvent was removed and to the residue was added ethyl acetate (250 ml). The mixture was washed with water (250 ml), and then ethyl acetate was removed to give crude (R)-glycidylphthalimide (optical purity: 97% e.e.). The crude product was crystallized from ethyl acetate-hexane to give the object (R)-glycidylphthalimide (45.6 g, yield: 83%, optical purity: 98% e.e.) as white crystals. mp 100–102° C.

Specific rotation $[\alpha]_D^{25}$ −9.7° (c2.0. CHCl$_3$) $^1$HNMR (CDCl$_3$, 270 MHz) δ 2.70 (dd, 1H), 2.81 (dd, 1H), 3.21–3.28 (m, 1H), 3.81 (dd, 1H), 3.97 (dd, 1H), 7.27–7.91 (m, 4H)

The optical purity was calculated using HPLC and by its area ratio.

Condition:
Column: CHIRALPAC AD (0.46 cmΦ×25 cm L (Daicel Co., Ltd.)
Mobile phase: n-hexane/isopropanol (90/10 (v/v)
Velocity: 1.0 ml/min.
Detection: UV220 nm
Retention: (S) isomer=17.9 min., (R) isomer=25.5 min.

EXAMPLE 2

Into a reaction vessel were put potassium phthalimide (5.00 g, 27.0 mmol), benzyltrimethylammonium chloride (0.50 g, 2.70 mmol) and tert-buyl alcohol (50 ml) and then thereto was added (S)-epichlorohydrin (6.53 g, 54.0 mmol). The mixture was stirred at 20° C. for 24 hours and the solvent was removed. To the residue was added ethyl acetate (30 ml), the mixture was washed with water (20 ml), and then ethyl acetate was removed to give crude (S)-glycidylphthalimide (3.95 g, yield: 72%, optical purity: 97% e.e.) as a white solid.

EXAMPLE 3

Into a reaction vessel were put potassium phthalimide (5.00 g, 27.0 mmol), benzyltrimethylammonium chloride (0.50 g, 2.70 mmol) and methanol (50 ml) and then thereto was added (R)-epichlorohydrin (9.99 g, 81.0 mmol). The mixture was stirred at 20° C. for 15 hours and the solvent was removed. To the residue was added ethyl acetate (30 ml), the mixture was washed with water (20 ml) and ethyl acetate was removed to give crude (R)-glycidylphthalimide (3.74 g, yield: 68%, optical purity: 99% e.e.) as a white solid.

COMPARATIVE EXAMPLE 1

Into a reaction vessel were put potassium phthalimide (5.00 g, 27.0 mmol), benzyltrimethylammonium chloride (0.50 g, 2.70 mmol) and DMF (50 ml) and then thereto was added (R)-epichlorohydrin (5.00 g, 54.0 mmol). The mixture was stirred at room temperature for 16 hours and the solvent was removed. To the residue was added ethyl acetate (30 ml), the mixture was washed with water (20 ml) and ethyl acetate was removed to give crude (R)-glycidylphthalimide (4.48 g, yield: 82%, optical purity: 63% e.e.) as a white solid.

Comparative examples 2–4 were shown in the following Table 1, which were conducted by changing the solvent according to the method of Comparative example 1.

TABLE 1

|  | Solvent | Reaction temp/hr | Yield | Optical purity (% ee) |
|---|---|---|---|---|
| Comp. ex. 2 | THF | 50° C./44 hr | 74 | 87 |
| Comp. ex. 3 | Toluene | 50° C./20 hr | n.d | n.d. |
| Comp. ex. 4 | 1,2-Dichloroethane | 30° C./16 hr | n.d. | n.d. |

EXAMPLE 4

Into a reaction vessel were put phthalimide (200.0 g, 1.36 mol), (S)-epichlorohydrin (226.4 g, 2.45 mol), anhydrous sodium carbonate (14.40 g, 0.136 mol), benzyltrimethylammonium chloride (25.24 g, 0.136 mol) and isopropanol (1.2 L) and the mixture was reacted at 25° C. for 22 hours to give crude N-(3-chloro-2-hydroxypropyl)phthalimide. The reaction mixture is cooled to 15° C. and then thereto was dropped a mixture of potassium tert-butoxide (183.0 g, 1.63 mol) and isopropanol (0.8 L) over a two hours period and the mixture was stirred for 2 hours at the same temperature. The solvent was removed and to the residue was added ethyl acetate (1.3 L). The mixture was washed with water (0.65 L), and then ethyl acetate was removed to give crude (S)-glycidylphthalimide. The crude product was crystallized from ethyl acetate-hexane to give the object (S)-glycidylphthalimide (206.3 g, yield: 75%, optical purity: 98% e.e.) as white crystals. mp 99–101° C.

Specific rotation $[\alpha]_D^{25}$+11.00 (c2. o, CHCl$_3$) N-(3-Chloro-2-hydroxypropyl)phthalimide $^1$HNMR (CDCl$_3$, 270 MHz) δ 2.83 (d, 1H), 3.58–3.73 (m, 2H), 3.85–4.01 (m, 2H), 4.13–4.21 (m, 1H), 7.73–7.89 (m, 4H)

EXAMPLE 5

Into a reaction vessel were put phthalimide (2.00 g, 13.6 mol), (R)-epichlorohydrin (2.52 g, 27.2 mol), anhydrous sodium carbonate (144 mg, 1.36 mol), benzyltrimethylammonium chloride (252 mg, 1.36 mol) and isopropanol (13 ml) and the mixture was reacted at room temperature for 15 hours. After removal unreacted epichlorohydrin, to the residue was added isopropanol (13 ml) and the mixture is cooled to 20° C. Then thereto was gradually dropped a mixture of potassium tert-butoxide (1.83 g, 16.3 mol) and isopropanol (7 ml) and the mixture was stirred for 1 hour at the same temperature. The solvent was removed and to the residue was added ethyl acetate (13 ml). The mixture was washed with water (7 ml), and then ethyl acetate was removed to give crude (R)-glycidylphthalimide (2.16 g, yield 78%, optical purity 98% e.e.) as white crystals.

In the same manner as Example 5, the following Examples were conducted by using an alkali metal carbonate or an alkali metal hydrogencarbonate with benzyltrimethylanmonium chloride.

TABLE 2

|  | Absolute configuration of epichlorohydrin | Organic solvent | Carbonate or Hydrogencarbonate | Reaction temp. at 1st step | Glycidyl phthalimide | |
|---|---|---|---|---|---|---|
|  |  |  |  |  | Yield | Optical purity (a.c.) |
| Ex. 6 | (S) | t-Butanol | Na$_2$CO$_3$ | Room temp./23 hr | 84% | 98% ee (S) |
| Ex. 7 | (R) | Methanol | Na$_2$CO$_3$ | Room temp./43 hr | 61% | 98% ee (R) |
| Ex. 8 | (R) | THF | Na$_2$CO$_3$ | 50° C./39 hr | 81% | 97% ee (R) |
| Ex. 9 | (R) | isopropanol | Li$_2$CO$_3$ | Room temp./22 hr | 77% | 98% ee (R) |
| Ex. 10 | (R) | isopropanol | K$_2$CO$_3$ | Room temp./23 hr | 75% | 98% ee (R) |
| Ex. 11 | (R) | isopropanol | Cs$_2$CO$_3$ | Room temp./22 hr | 70% | 98% ee (R) |
| Ex. 12 | (R) | isopropanol | NaHCO$_3$ | Room temp./25 hr | 80% | 98% ee (R) |
| Ex. 13 | (R) | isopropanol | only Q.A.S. | 40° C./22 hr | 90% | 98% ee (R) |

Note:
in Example 13, only benzyltrimethylanmonium chloride was used as a quaternary ammonium salt (Q.A.S). In Example 7, sodium methoxide (in 28% methanol solution) was used as an alkali metal alkoxide, and in Example 8 potassium tert-butoxide, itself was added in several divided potions.

Note: in Example 13, only benzyltrimethylanmonium chloride was used as a quaternary ammonium salt (Q.A.S). In Example 7, sodium methoxide (in 28% methanol solution) was used as an alkali metal alkoxide, and in Example 8 potassium tert-butoxide, itself was added in several divided position.

EXAMPLE 14

Into a reaction vessel were put phthalimide (2.00 g, 13.6 mol), (R)-epichlorohydrin (2.26 g, 24.5 mmol), anhydrous sodium carbonate (0.72 g, 6.80 mmol), tetra n-butylammonium hydrogensulfate (0.46 g, 1.36 mol) and isopropanol (13 ml) and the mixture was reacted at room temperature at 50° C. for 23 hours. And then to the residue was gradually added potassium tert-butoxide (1.83 g, 16.3 mmol) in isopropanol and the mixture is stirred at 20° C. for 1 hour. After the reaction, post-treatment was carried out to give crude (R)-glycidylphthalimide (2.21 g, yield 80%, optical purity 98% e.e.) as white crystals.

COMPARATIVE EXAMPLE 5

Into a reaction vessel were put phthalimide (2.00 g, 13.6 mmol), benzyltrimethylammonium chloride (252 mg, 1.36 mol) and isopropanol (25 mL) and the mixture was ice cooled. Thereto were added potassium tert-butoxide (3.05 g, 27.2 mmol) in several divided portions and then (R)-epichlorohydrin (2.52 g, 27.2 mmol). The mixture was reacted at room temperature for 26 hours and then post-treatment was carried out to give crude (R)-glycidylphthalimide (0.45 g, yield 17%, optical purity 96% e.e.) as a yellow highly viscous product.

According to the present inventions, there are easily obtainable glycidylphthalimide, especially its optically active compound in good yield with optically high purity and also a N-(3-halo-2-hydroxypropyl)phthalimide, especially its optically active compound in good yield with optically high purity.

The present invention being thus described, it will be obvious that the same may be varied in many ways. Such variations are not to be regarded as a departure from the scope of the present invention, and all such modifications as would be obvious to one skilled in the art are intended to be included within the scope of the following claims.

What is claimed is:

1. A process for preparing glycidylphthalimide represented by the following formula (1):

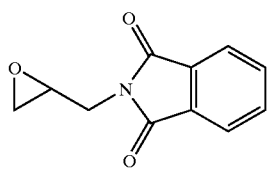

(1)

which comprises reacting in an alcohol solvent an alkali metal phthalimide represented by the following formula (2):

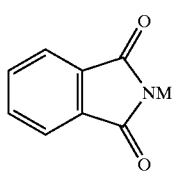

(2)

wherein M is an alkali metal,
with an epihalohydrin represented by the following formula (3):

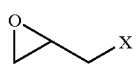

(3)

wherein X is a halogen atom; or reacting phthalimide and an epihalohydrin (3) in an organic solvent in the presence of an alkali metal carbonate, an alkali metal hydrogencarbonate or a quatenary ammonium salt (4) represented by the following formula:

$$R_1 R_2 R_3 R_4 N^+ X^-$$ (4)

wherein $R_1$, $R_2$, $R_3$ and $R_4$ are the same or different, $C_{1-16}$ alkyl, $C_{2-46}$ alkenyl, aryl-alkyl($C_{1-16}$) or aryl, and X is chloro ion, bromo ion, iodo ion, hydrogensulfate ion or hydroxy ion, to prepare a N-(3-halogeno-2-hydroxypropyl)phthalimide represented by the following formula (5):

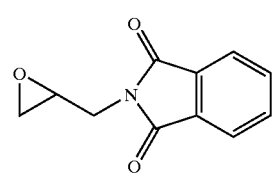

(1)

wherein X is the same as defined above,
cyclizing the compound (5) with an alkali metal alkoxide, and recovering the resultant glycidylphthalimide.

2. A process for preparing glycidylphthalimide represented by the following formula (1):

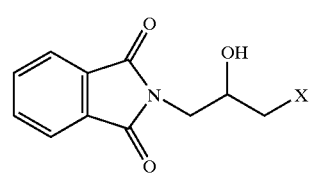

(5)

which comprises reacting in an alcohol solvent an alkali metal phthalimide represented by the following formula (2):

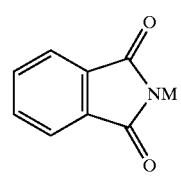

(2)

wherein M is an alkali metal,
with an epihalohydrin represented by the following formula (3):

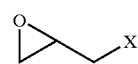

(3)

wherein X is a halogen atom, and recovering the resultant glycidylphthalimide.

3. The process claimed in claim 2 wherein the epihalohydrin is an optically active epihalohydrin, and the glycidylphthalimide is optically active glycidylphthalimide.

4. The process claimed in claim 2 wherein the reaction is carried out in the presence of a quaternary ammonium salt of the formula (4):

$$R_1 R_2 R_3 R_4 N^+ X^-$$ (4)

wherein $R_1$, $R_2$, $R_3$ and $R_4$ are the same or different, $C_{1-16}$ alkyl, $C_{2-16}$ alkenyl, aryl-alkyl($C_{1-16}$) or aryl, and X is chloro ion, bromo ion, iodo ion, hydrogensulfate ion or hydroxy ion.

5. The process claimed in claim 2 wherein the halogen atom in the epihalohidorin is a chlorine atom.

6. The process claimed in claim 2 wherein the alkali metal phthalimide is potassium phthalimide.

7. The process claimed in claim 2 wherein the alcohol solvent is a secondary alcohol or a tertiary alcohol.

8. A process for preparing glycidylphthalimide represented by the following formula (1):

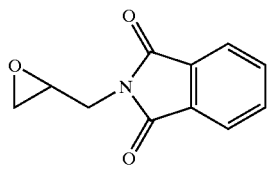
(1)

which comprises reacting phthalimide and an epihalohydrin represented by the following formula (3):

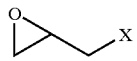
(3)

wherein X is a halogen atom, in an organic solvent in the presence of an alkali metal carbonate, an alkali metal hydrogencarbonate or a quatenary ammonium salt (4) represented by the following formula:

$$R_1\ R_2\ R_3\ R_4\ N^+X^- \qquad (4)$$

wherein $R_1$, $R_2$, $R_3$ and $R_4$ are the same or different, $C_{1-16}$ alkyl, $C_{2-16}$ alkenyl, aryl-alkyl($C_{1-16}$) or aryl, and X is chloro ion, bromo ion, iodo ion, hydrogensulfate ion or hydroxy ion, to prepare a N-(3-halogeno-2-hydroxypropyl)phthalimide represented by the following formula (5):

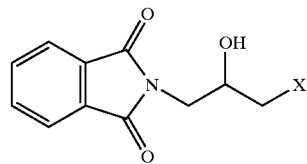
(5)

wherein X is the same defined above, cyclizing the compound (5) with an alkali metal alkoxide, and recovering the resultant glycidylphthalimide.

9. The process claimed in claim 8 wherein the reaction of the first step and the second step is carried out in one pot.

10. The process claimed in claim 8 wherein the epihalohydrin is an optically active epihalohydrin, and the glycidylphthalimide is optically active glycidylphthalimide.

11. The process claimed in claim 8 wherein the halogen atom in the epihalohidorin is a chlorine atom.

12. The process claimed in claim 8 wherein the organic solvent is an alcohol or an ether.

13. The process claimed in claim 12 wherein the alcohol is methanol, isopropanol or tert-butanol, and the ether is tetrahydrofuran or 1,4-dioxane.

14. The process claimed in claim 3 wherein the reaction is carried out in the presence of a quaternary ammonium salt of the formula (4):

$$R_1\ R_2\ R_3\ R_4\ N^+X^- \qquad (4)$$

wherein $R_1$, $R_2$, $R_3$ and $R_4$ are the same or different, $C_{1-16}$ alkyl, $C_{2-16}$ alkenyl, aryl-alkyl($C_{1-16}$) or aryl, and X is chloro ion, bromo ion, iodo ion, hydrogensulfate ion or hydroxy ion.

15. The process claimed in claim 3 wherein the halogen atom in the optically active epihalohydrin is a chlorine atom.

16. The process claimed in claim 3 wherein the alkali metal phthalimide is potassium phthalimide.

17. The process claimed in claim 3 wherein the alcohol solvent is a secondary alcohol or a tertiary alcohol.

18. The process claimed in claim 10 wherein the halogen atom in the optically active epihalohydrin is a chlorine atom.

19. The process claimed in claim 10 wherein the organic solvent is an alcohol or an ether.

20. The process claimed in claim 19 wherein the alcohol is methanol, isopropanol or tert-butanol, and the ether is tetrahydrofuran or 1,4-dioxane.

* * * * *